(12) United States Patent
Li et al.

(10) Patent No.: US 9,136,184 B2
(45) Date of Patent: Sep. 15, 2015

(54) IN SITU OPTICAL DIAGNOSTIC FOR MONITORING OR CONTROL OF SODIUM DIFFUSION IN PHOTOVOLTAICS MANUFACTURING

(75) Inventors: Jian Li, Golden, CO (US); Dean Levi, Indian Hills, CO (US); Miguel Contreras, Golden, CO (US); Stephen Glynn, Boulder, CO (US)

(73) Assignee: Alliance For Sustainable Energy, LLC, Golden, CO (US)

( * ) Notice: Subject to any disclaimer, the term of this patent is extended or adjusted under 35 U.S.C. 154(b) by 12 days.

(21) Appl. No.: 14/112,033

(22) PCT Filed: Feb. 17, 2012

(86) PCT No.: PCT/US2012/025631
§ 371 (c)(1),
(2), (4) Date: Oct. 15, 2013

(87) PCT Pub. No.: WO2012/112880
PCT Pub. Date: Aug. 23, 2012

(65) Prior Publication Data
US 2014/0093985 A1    Apr. 3, 2014

Related U.S. Application Data

(60) Provisional application No. 61/444,499, filed on Feb. 18, 2011.

(51) Int. Cl.
*H01L 21/66* (2006.01)
*G01N 21/21* (2006.01)
(Continued)

(52) U.S. Cl.
CPC *H01L 22/10* (2013.01); *G01N 9/00* (2013.01); *G01N 21/211* (2013.01);
(Continued)

(58) Field of Classification Search
CPC ................. H01L 29/41733; H01L 31/022425; H01L 27/14692; H01L 21/02614; H01L 21/707; H01L 29/78633; Y02E 10/543
See application file for complete search history.

(56) References Cited

U.S. PATENT DOCUMENTS 4,422,159 A * 12/1983 Craighead et al. ............ 365/127
5,441,897 A   8/1995 Noufi et al.
(Continued)

OTHER PUBLICATIONS

Al-Thani et al., "The Deposition and Characterization of Mo/CuInGaSe2/CdS/ZnO Solar Cells", Conference Paper—Sharjah Solar Energy Conference, Jan. 2001, pp. 1-11, http://www.nrel.gov/docs/fy01osti/29641.pdf.
(Continued)

*Primary Examiner* — Evan Pert
*Assistant Examiner* — Gustavo Ramallo
(74) *Attorney, Agent, or Firm* — John C. Stolpa; Suzanne C. Walts

(57) ABSTRACT

A method of fabricating a photovoltaic device 100, includes the steps of providing a glass substrate 102, depositing a molybdenum layer 104 on a surface of the glass substrate, directing light through the glass substrate to the near-substrate region of the molybdenum layer 206, detecting an optical property of the near-substrate region of the molybdenum layer after interaction with the incident light 208 and determining a density of the near-substrate region of the molybdenum layer from the detected optical property 210. A molybdenum deposition parameter may be controlled based upon the determined density of the near-substrate region of the molybdenum layer 218. A non-contact method measures a density of the near-substrate region of a molybdenum layer and a deposition chamber 300.

24 Claims, 5 Drawing Sheets

(51) Int. Cl.
*G01N 21/84* (2006.01)
*H01L 31/0392* (2006.01)
*G01N 9/00* (2006.01)
*H01L 31/18* (2006.01)

(52) U.S. Cl.
CPC ........... *G01N 21/8422* (2013.01); *H01L 22/12* (2013.01); *H01L 31/03923* (2013.01); *H01L 31/18* (2013.01); *G01N 2021/213* (2013.01); *Y02E 10/541* (2013.01)

(56) References Cited

U.S. PATENT DOCUMENTS

| | | | |
|---|---|---|---|
| 6,362,881 B1 | 3/2002 | Pickering et al. | |
| 6,518,086 B2 | 2/2003 | Beck et al. | |
| 6,566,162 B2 | 5/2003 | Yamada et al. | |
| 7,732,229 B2 | 6/2010 | Leidholm et al. | |
| 7,875,945 B2* | 1/2011 | Krasnov et al. | 257/436 |
| 8,071,419 B2 | 12/2011 | Robinson et al. | |
| 8,197,885 B2* | 6/2012 | Honecker et al. | 427/74 |
| 2003/0052382 A1 | 3/2003 | Stanbery | |
| 2005/0089761 A1* | 4/2005 | Sugawara | 430/5 |
| 2007/0040172 A1* | 2/2007 | Kawakami et al. | 257/59 |
| 2007/0177481 A1 | 8/2007 | Kimura et al. | |
| 2007/0189956 A1 | 8/2007 | Geyer et al. | |
| 2007/0213954 A1* | 9/2007 | Price | 702/172 |
| 2007/0287209 A1* | 12/2007 | Fujii | 438/26 |
| 2008/0006844 A1 | 1/2008 | D'Evelyn et al. | |
| 2008/0232755 A1* | 9/2008 | Kabir | 385/131 |
| 2008/0302418 A1 | 12/2008 | Buller et al. | |
| 2010/0044676 A1 | 2/2010 | Sargent et al. | |
| 2010/0091153 A1 | 4/2010 | Ogasawara et al. | |
| 2010/0269907 A1* | 10/2010 | Lackner et al. | 136/264 |
| 2011/0024859 A1 | 2/2011 | Miyazaki et al. | |
| 2011/0030800 A1 | 2/2011 | Fujdala et al. | |
| 2011/0034640 A1 | 2/2011 | Fujdala et al. | |
| 2011/0041918 A1 | 2/2011 | Fujdala et al. | |
| 2011/0108115 A1 | 5/2011 | Deligianni et al. | |
| 2011/0290641 A1* | 12/2011 | Weiner et al. | 204/275.1 |
| 2012/0006102 A1 | 1/2012 | Bryant et al. | |
| 2012/0133853 A1* | 5/2012 | Ito et al. | 349/38 |

OTHER PUBLICATIONS

Al-Thani et al., The Effect of Mo Back Contact on Na Out-Diffusion and Device Performance of Mo/Cu(In, Ga)Se2/CdS/ZnO Solar Cells, Conference Paper, May 2002, 29th IEEE PV Specialists Conference, pp. 1-4, http://www.nrel.gov/docs/fy02osti/32254.pdf.
Contreras et al., "Progress Toward 20% Efficiency in Cu(In, Ga)Se2 Polycrystalline Thin-film Solar Cells", Progress in Photovoltaics: Research and Applications, 1999, vol. 7, No. 4, pp. 311-316.
Katagiri et al., "Development of CZTS-based Thin Film Solar Cells", Thin Solid Films, 2009, vol. 517, pp. 2455-2460.
Li et al., "Density Profiles in Sputtered Molybdenum Thin Films and Their Effects on Sodium Diffusion in Cu(InxGa1-x) Se2 Photovoltaics", Conference Paper, 37th IEEE Photovoltaics Specialists Conference, Jul. 2011, pp. 1-4.
Nukala et al., "Synthesis of Optimized CZTS Thin Films for Photovoltaic Absorber Layers by Sputtering from Sulfide Targets and Sulfurization", Materials Research Society Symposium Proceedings, 2010, vol. 1268, pp. 1-6.
Pennycook et al., "High-Resolution Incoherent Imaging of Crystals", Physical Review Letters, Feb. 19, 1990, vol. 64, No. 8, pp. 938-942.
Prabhakar, "Effect of sodium Diffusion on the Structural and Electrical Properties of Cu2ZnSnS4 Thin Films", Solar Energy Materials & Solar Cells, 2011, vol. 95, pp. 1001-1004.
Scofield et al., "Sputtered Molybdenum Bilayer Back Contact for Copper Indium Diselenide-Based Polycrystalline Thin-Film Solar Cells", Thin Solid Films, 1995, vol. 260, pp. 26-31.
International Search Report for International (PCT) Application No. PCT/US12/25631, mailed May 25, 2012, pp. 1-3.
Written Opinion for International (PCT) Application No. PCT/US12/25631, mailed May 25, 2012, pp. 1-5.
International Preliminary Report on Patentability for International (PCT) Application No. PCT/US12/25631, issued Aug. 21, 2013, pp. 1-6.

* cited by examiner

IN SITU OPTICAL DIAGNOSTIC FOR MONITORING OR CONTROL OF SODIUM DIFFUSION IN PHOTOVOLTAICS MANUFACTURING

The United States Government has rights in this invention under Contract No. DE-AC36-08GO28308 between the United States Department of Energy and the Alliance for Sustainable Energy, LLC, the manager and operator of the National Renewable Energy Laboratory.

BACKGROUND

Thin film photovoltaics (PV) based on $Cu(In_xGa_{1-x})Se_1$ (CIGS) and similar technologies such as $Cu_2ZnSnS_4$ (CZTS) or $Cu_2ZnSnSe_4$ (CZTSe) are promising candidates for low-cost, high-efficiency solar cell applications. CIGS technology has demonstrated the highest energy conversion efficiency among all thin film PV technologies. The most commonly used substrate for CIGS, CZTS, CZTSe or similar PV cells is inexpensive and readily available soda lime glass (SLG) coated with a molybdenum thin film as the back metal contact. The molybdenum layer also reflects unabsorbed light back into the PV absorber layers.

An important process associated with the above classes of solar cells is sodium (Na) diffusion from the SLG substrate through the molybdenum back contact layer into the CIGS or similar absorber layer. Devices are fabricated by first depositing a thin film of molybdenum, typically about 500 nm in thickness, on a sheet of SLG, followed by deposition of the CIGS active layer onto the molybdenum film. Sodium diffuses from the SLG, through the molybdenum, and into the CIGS layer. This sodium acts as an electronic dopant in the CIGS layer and may have an impact on the device performance and final conversion efficiency.

The properties of the molybdenum film may play a role in determining the extent and characteristics of sodium diffusion from the SLG substrate into the absorber layer of a solar cell. Proper sodium concentration in the absorber layer may help to optimize the performance of a solar cell based on CIGS or similar technologies. At this time, the factors controlling sodium diffusion are not well known. Thus, process variations in the deposition of the molybdenum layer can produce what appear to be uncontrolled variations in device performance. Typically, CIGS cell manufacturers have assumed that the molybdenum films are constant in density and thus it is only the thickness of the molybdenum film that determines the extent and characteristics of sodium diffusion. This assumption has lead to the use of X-ray fluorescence (XRF) as the standard diagnostic measure of molybdenum films in CIGS or similar solar cell manufacturing.

This reliance upon molybdenum layer thickness as a controlled device fabrication parameter may cause production problems however, since most CIGS PV manufacturers are not aware that relatively small variations in molybdenum deposition conditions can cause large variations in the amount of sodium diffusion into the CIGS film. The unexpected and unknown variations in sodium diffusion can interact with and amplify variations in subsequent processing steps. This in turn may lead to reductions in manufacturing yields because of uncontrolled and unexplained variations in CIGS film properties and device performance.

The foregoing examples of the related art and limitations related therewith are intended to be illustrative and not exclusive. Other limitations of the related art will become apparent to those of skill in the art upon a reading of the specification and a study of the drawings.

SUMMARY OF THE EMBODIMENTS

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One embodiment is a method of measuring a density of the near-substrate region of a molybdenum layer deposited on a glass substrate. The method includes providing a glass substrate having a molybdenum layer deposited on a surface of the glass substrate, directing light through the substrate to a near-substrate region of the molybdenum layer and detecting an optical property of the near-substrate region of the molybdenum layer after interaction with the incident light. The method further includes determining a density of the near-substrate region of the molybdenum layer from the detected optical property. As used herein, the term "near-substrate region" is defined as the region of the molybdenum contact layer that is adjacent the glass substrate layer. Thus, the near-substrate region of the molybdenum layer is the first portion of the molybdenum layer deposited upon the substrate during device fabrication. The near-substrate region may be, for example, the first 20 nm, 30 nm, 40 nm, 50 nm, 60nm, 70 nm, 80 nm, 90 nm or 100 nm deposited adjacent the glass substrate.

The method of measuring a density of the near-substrate region of a molybdenum layer may further include the step of directing light having one or more predetermined wavelengths through the substrate to the near-substrate region of the molybdenum layer. The light detected after interaction with the molybdenum layer may be analyzed by any known optical means to determine an optical property of the near-substrate region of the molybdenum layer, including but not limited to, detecting a change in light polarization or a change in light intensity. The optical property of the near-substrate region of the molybdenum layer may be determined by any suitable method including, but not limited to, non-spectroscopic ellipsometry, non-spectroscopic reflectivity, non-spectroscopic transmission, spectroscopic ellipsometry, spectroscopic reflectivity, spectroscopic transmission or other means.

The disclosed methods are well suited to in-line or in-situ fabrication processes. Therefore, the disclosed methods may be implemented by directing light through the substrate to the near-substrate region of the molybdenum layer as the glass substrate moves in a fabrication process line.

An alternative embodiment is a method of fabricating a photovoltaic device including the steps of providing a glass substrate, depositing a molybdenum layer on a surface of the glass substrate, directing light through the substrate to a near-substrate region of the molybdenum layer, detecting an optical property of the near-substrate region of the molybdenum layer after interaction with the incident light and determining a density of the near-substrate region of the molybdenum layer from the detected optical property. This embodiment may further include the step of controlling a molybdenum deposition parameter based upon the determined density of the near-substrate region of the molybdenum layer. The controlled molybdenum deposition parameter may be, for example, deposition temperature, deposition power density, deposition power, deposition current, deposition voltage, deposition atmosphere flow rate and deposition atmosphere pressure.

Fabrication method embodiments may also include the steps of depositing an active absorber layer above the molybdenum layer and controlling sodium diffusion through the molybdenum layer by controlling the density of a near-substrate region of the molybdenum layer. The active absorber layer may be a $Cu(In_xGa_{1-x})Se_2$ (CIGS) layer or a layer associated with similar technologies, such as $Cu_2ZnSnS_4$ (CZTS) or $Cu_2ZnSnSe_4$ devices (CZTSe). In addition to controlling a molybdenum deposition parameter in view of the determined near-substrate region molybdenum density the active layer composition or selected active layer deposition parameters may be controlled in response to the determined density of the near-substrate region of the molybdenum layer.

An alternative embodiment is a deposition chamber including, a gas inlet and outlet, a molybdenum target providing for the deposition of a molybdenum layer on a glass substrate, a substrate transport system, a light source providing for the illumination of a near-substrate region of the molybdenum layer deposited on the glass substrate and a detector in optical communication with the light after interaction with the near-substrate region of the molybdenum layer. A deposition chamber embodiment may also include a processor in digital communication with the detector, the processor being configured to determine a density of the near-substrate region of the molybdenum layer from a detected optical property. The processor may be further configured to control a deposition parameter in response to the determined density of the near-substrate region of the molybdenum layer as described above.

In addition to the exemplary aspects and embodiments described above, further aspects and embodiments will become apparent by reference to the drawings and by study of the following descriptions.

BRIEF DESCRIPTION OF THE DRAWINGS

Exemplary embodiments are illustrated in referenced figures of the drawings. It is intended that the embodiments and figures disclosed herein are to be considered illustrative rather than limiting.

DETAILED DESCRIPTION

Unless otherwise indicated, all numbers expressing quantities of ingredients, dimensions, reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Certain abbreviations may be made herein with respect to the description of semiconductors and semiconductor alloys. These abbreviations shall not be construed as limiting the scope of the disclosure or claims. For example, the form CIGS is a commonly used abbreviation to improve readability in technical manuscripts. Abbreviated forms such as "CIGS" are defined as equivalent to an expanded form, for example; "$Cu(In_xGa_{1-x})Se_2$".

Figure 1:
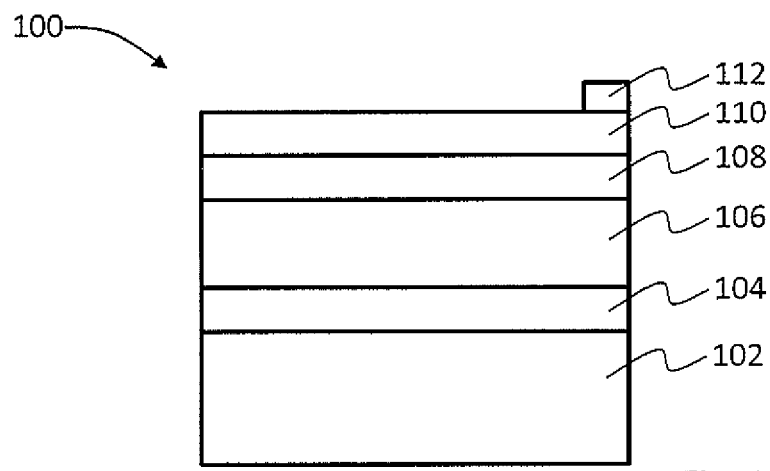
FIG. 1 illustrates a simplified schematic diagram of a solar cell having a glass substrate and a molybdenum back contact.

The embodiments disclosed herein relate to thin film photovoltaics (PV) having active regions of $Cu(In_xGa_{1-x})Se_2$ (CIGS) or similar technologies such as $Cu(In_xGa_{1-x})S_ySe_{2-y}$ (CIGSS), $Cu_2ZnSnS_4$ photovoltaic devices (CZTS), $Cu_2ZnSnSe_4$ devices (CZTSe), or CdTe. The foregoing classes of PV devices are commonly referred to as solar cells. Although the embodiments described in detail below are described with respect to a CIGS cell, the scope of this disclosure is intended to encompass similar PV technologies. CIGS PV devices are typically manufactured on a glass substrate which is often, but not always a soda lime glass (SLG) substrate. A typical CIGS solar cell is schematically illustrated in FIG. 1 and is composed of at least one active semiconductor layer and associated substrate, window and contact layers. The embodiments disclosed herein are described with reference to a typical and highly simplified CIGS solar cell such as illustrated in FIG. 1. It is important to note however, that the various methods and systems described are not limited specifically to CIGS cells. The recited methods and systems are applicable to any PV device or solar cell which relies upon, is enhanced by or features sodium diffusion from a glass substrate through a metal contact, for example a molybdenum (Mo) contact to an active layer.

As illustrated in FIG. 1, a simplified CIGS solar cell 100 may include a glass substrate, which is typically a SLG substrate 102. An approximately 300 nm-1000 nm thick molybdenum back contact 104 may be deposited on the SLG substrate 102. A CIGS active absorber layer 106 may be deposited or gown on the molybdenum back contact layer 104. The solar cell may be completed with a thin n-type buffer, such as a CdS layer 108, a ZnO window layer 110 and one or more front contacts 112. It is important to note that the CIGS solar cell 100, illustrated in FIG. 1 is highly simplified and an actual device may have various other active, buffer, window or other layers or regions, which are not illustrated for simplicity and clarity reasons. The simplified FIG. 1 solar cell 100 is shown to provide structural context for the discussion below concerning the effect of the properties of the molybdenum back contact layer 104 on device performance and methods of measuring and controlling selected molybdenum layer and sodium diffusion properties.

A process associated with the above classes of solar cells is sodium (Na) diffusion from the SLG substrate through the molybdenum back contact layer into the CIGS or similar absorber layer. The diffused sodium acts as an electronic dopant in the CIGS layer. The amount of sodium that diffuses into the CIGS film may have an effect on CIGS PV module efficiency; hence accurate control of sodium diffusion may be desirable for process control when manufacturing high performance CIGS PV modules. It is typically assumed that the molybdenum films are constant in density, and thus, it has generally only been the thickness of the molybdenum film that has been thought to determine sodium diffusion. This assumption has led to the use of X-ray fluorescence (XRF) as the standard diagnostic measure of molybdenum films in CIGS manufacturing. However, XRF is not sensitive to film density but, in only sensitive to the total number of atoms within the sampling volume. Thus, with XRF a manufacturer heretofore has generally assumed a constant density, and thus, inferred film thickness.

The various system and method embodiments disclosed herein are premised upon new discoveries regarding the molybdenum layer in a CIGS-type device. First, it has been demonstrated that molybdenum density may be determined with suitable accuracy through non-contact and rapid optical means. In addition, it has been discovered that a typical molybdenum layer deposited on a glass substrate by sputtering or an equivalent method will exhibit a density gradient with the densest molybdenum being in a "near-substrate region." As used herein, the term "near-substrate region" is defined as the region of the molybdenum contact layer that is adjacent the glass substrate layer. Thus, the near-substrate region of the molybdenum layer is the first portion of the molybdenum layer deposited upon the substrate during device fabrication. The near-substrate region may be, for example, the first 20 nm, 30 nm, 40 nm, 50 nm, 60 nm, 70 nm, 80 nm, 90 nm or 100 nm deposited adjacent the glass substrate.

As described in detail below, sputter-deposited molybdenum films are higher in density in the about 0-100 nm closest to the molybdenum-glass interface than in the remaining approximately 450 nm of molybdenum film. Another discovery underlying the embodiments disclosed herein is that the density of the near-substrate region of the molybdenum layer may play an important role in controlling sodium diffusion from the SLG substrate into the CIGS layer.

The foregoing discoveries may be applied to device fabrication techniques, because the density of the near-substrate region of the molybdenum film may vary significantly with deposition conditions. Because sodium may play an important role in the device performance of a CIGS or similar PV devices, variations in the near-substrate region of the molybdenum layer may interact with and amplify process variations in subsequent manufacturing steps.

As noted above, most CIGS manufacturers currently use X-ray fluorescence (XRF) to measure the thickness of molybdenum layers. In view of the newly discovered density gradient present in sputtered molybdenum films and in view of the overall potential effect of the density of the near-substrate layer upon sodium diffusion, it may be observed that using XRF to characterize molybdenum films in CIGS manufacturing may result in an uncontrolled process variable, the density of the lowest 30-100 nm of the molybdenum film.

Using current technologies, molybdenum film density could be estimated using transmission electron microscopy (TEM) on very small samples removed from the production line. Hence, known CIGS manufacturing processes are effectively blind to molybdenum layer density variations in the near-substrate region during production, because TEM measurements may take days to provide measurements over a microscopically small area. The in situ, non-contact optical measurement and control methods described herein may provide density information over large areas and may be implemented with respect to substrates moving in real time on a production line.

The optical properties of a molybdenum thin film, including but not limited to, complex dielectric function s, index of refraction n and extinction coefficient k are found to be very sensitive to the density of the film. Therefore, these or potentially other optical properties may be used as a reliable indicator to determine the density of a molybdenum film. In view of the correlation between the optical properties of a molybdenum layer and the layer density, any method that measures optical properties, such as ellipsometry, transmittance, or reflectance, may be used to determine the density of the film and with carefully selected optical probe wavelengths, these optical methods may be used to measure the density of the near-substrate region of the molybdenum film. Non-contact optical approaches may have the advantage of being easily incorporated in situ, in-line, and in real time, with a very short measurement time, for example less than 1 second.

One representative, but not limiting embodiment of a non-contact optical measurement probe may utilize a beam of polarized light transmitted through a glass substrate onto the molybdenum film. By monitoring the change of polarization state of the light upon reflection at the molybdenum/glass interface, the complex dielectric function $\in$ of the near-substrate region of the molybdenum film may be accurately determined. This in turn may provide an accurate measure of the density of the near-substrate region of the molybdenum film.

Alternative optical methods may be implemented to measure the density of the near-substrate region of a deposited molybdenum layer. Alternative methods may include, but are not limited to, standard spectroscopic ellipsometry, spectroscopic reflectivity, or spectroscopic transmission. It may also be possible to perform ellipsometry, reflectivity, or transmission at only one or a few wavelengths to obtain the same information without spectroscopy.

As noted above, the optical constants of the molybdenum film may be directly related to the density of the film. The optical constants may determine the optical reflectivity of the molybdenum/SLG substrate interface. By using an initial calibration process it may be possible to establish a correlation between the density of the molybdenum film and the reflective properties of the molybdenum/SLG substrate. For example, an optical beam of selected wavelength or wavelengths may be directed towards the back or lower side of the SLG glass substrate during the deposition of the molybdenum film. The selected wavelengths may be chosen such that the light only penetrates 30-100 nm into the molybdenum film. The intensity and/or polarization of the light reflected from or transmitted through the molybdenum film may be used to determine the density of the lowest 30-100 nm of molybdenum film. This measure of molybdenum density may be performed in real time during the molybdenum film deposition, or could also be performed immediately after molybdenum deposition and prior to CIGS deposition.

Thus, optical probing methods, such as ellipsometry, reflectance, and transmission, may have the advantage of implementation in situ and in-line while providing real-time quantitative response. In addition, the types of optical properties and testing methods noted above may be sensitive to molybdenum layer depth profiles, and thus may be uniquely useful for studying thin film materials.

As noted above, sodium diffusion may be closely correlated with the density of the near-substrate region of the molybdenum layer. Thus, the methods described herein for molybdenum layer density control may directly impact sodium diffusion characteristics. In particular, sodium diffusion from the SLG substrate into the CIGS layer may be predicted, monitored, and controlled in situ, in-line, and in real time at a CIGS PV manufacturing plant using the techniques disclosed herein. Enhanced process control provided by the disclosed optical methods may enhance solar cell production yield, reduce product variability and increase module efficiency.

In particular, molybdenum density in the near-substrate region may be determined and compared with the target density of molybdenum for the particular manufacturing process. Different manufacturing processes may have different optimum target densities which may be determined by pre-production analysis. Once measured, density information may be used in several subsequent determinations, including but not limited to the following: If the density deviates only slightly from the target density, the downstream CIGS deposition process may be slightly modified to accommodate the difference in sodium diffusion properties of the molybdenum film using process loop control. If the density deviation is somewhat greater, but still within nominal limits, the deposition parameters of the molybdenum film may be adjusted in real time to bring the molybdenum density back to the target value. Finally, if the molybdenum density is outside of nominal limits, the substrate may be rejected from the manufacturing process. Another use of disclosed apparatus may be the commissioning of new equipment. An optical sensing system as described herein may be installed when new equipment is being brought online and used in the tuning and adjustment process until the operators are confident that they have determined the correct deposition parameters to achieve the desired Mo density profile. As part of the commissioning process optical measurements may be used to determine the range of tolerance to variations in the Mo deposition parameters that still produce the desired density profile of Mo. Once a robust set of deposition conditions is determined the sensor could be removed for use on another piece of equipment. In this manner the plant operators may accomplish the commissioning of a manufacturing process that is so robust that inline monitoring may not be deemed necessary.

Figure 2:
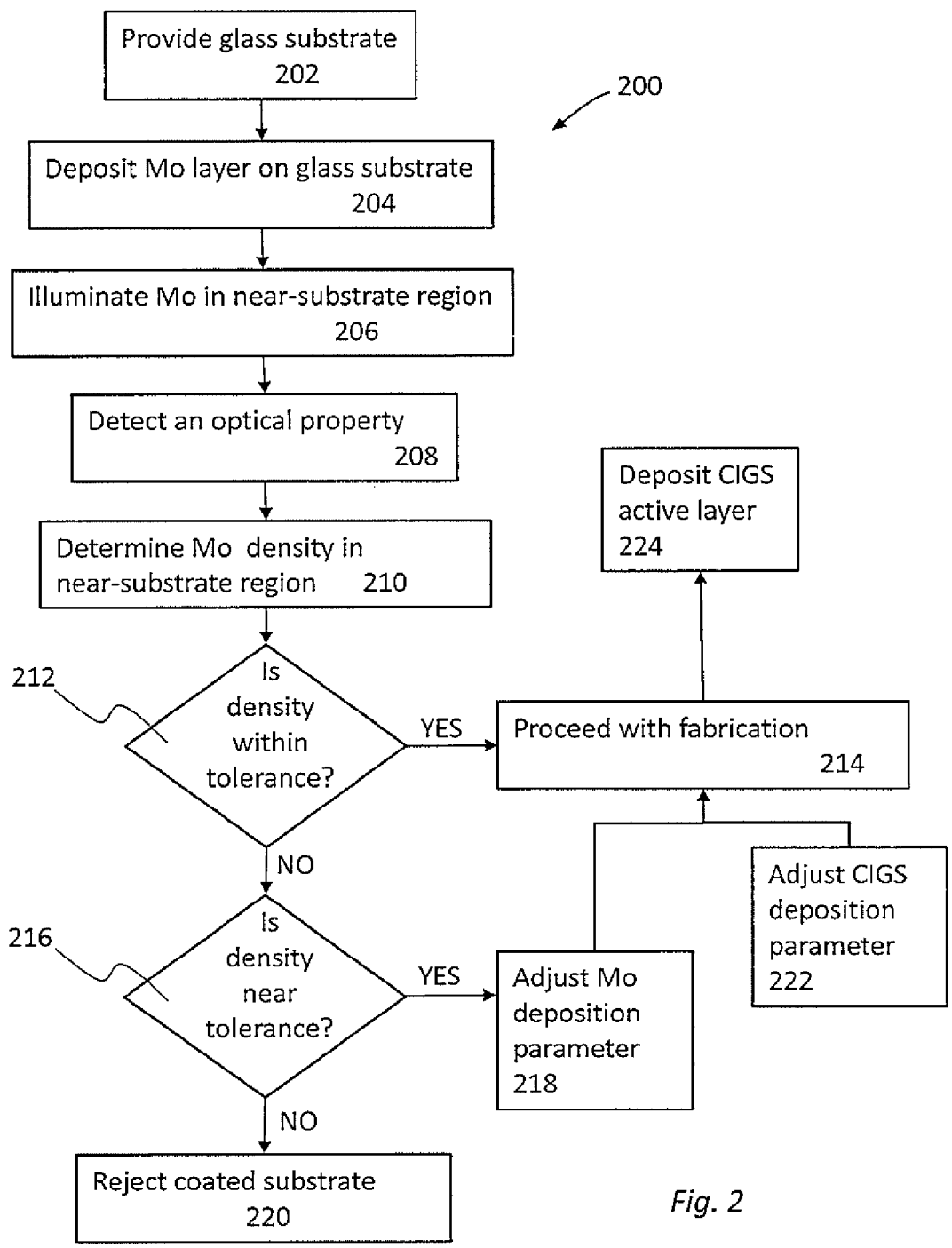
FIG. 2 illustrates a flow chart representation of a method as disclosed herein.

The foregoing observations lead to a non-limiting example PV fabrication process 200, as illustrated in FIG. 2. The process illustrated in FIG. 2 may begin with the provision of a suitable glass substrate (Step 202). A suitable substrate is typically SLG, but could be another suitable variety of glass. Next, a back contact layer of a metal, typically molybdenum, may be deposited on the glass substrate (Step 204). The molybdenum may be deposited by any suitable technique including, but not limited to sputter deposition. The near-substrate region may be illuminated with light functioning as an optical probe, either after the molybdenum is deposited, or during the molybdenum deposition process (Step 206). Illumination may be at one or more selected wavelengths and possibly selected polarization to facilitate ellipsometry or reflected or transmitted light analysis. The wavelengths used in the optical probe may be selected to confine detection to the near-substrate region of the molybdenum film or to maximize sensitivity to molybdenum density with the fewest wavelengths possible in order to simplify the system and minimize cost.

It has been found convenient to utilize light transmitted through the substrate to the near-substrate region of the film and then reflected back out through the substrate, but light could be transmitted through both the substrate and film from either side. After the light interacts with the molybdenum in the near-substrate region and is reflected or transmitted as desired, the light is detected by a suitable photodetector (Step 208). The detected light may then be analyzed to determine an optical property of the near-substrate region of the molybdenum layer after interaction with the incident light and thereby determine the density of the molybdenum in the near-substrate region as described above (Step 210).

The density of the near-substrate region may be utilized to monitor and control subsequent processes. For example, as shown on FIG. 2, the density may be compared to specific tolerances pre-determined to be necessary for the production of high-quality devices (Step 212). If the molybdenum density in the near-substrate region is suitable, additional fabrication steps may begin or continue (Step 214). Alternatively, if the near-substrate density is close to the ideal, but slightly out of tolerance, an adjustment to a deposition parameter may be made to tune the density of the molybdenum layer applied to subsequent substrates (Steps 216 and 218). If the density is far out of tolerance the particular substrate may be rejected and adjustments may be made to a deposition parameter to correct the density of the molybdenum layer applied to subsequent substrates (Steps 220, 218).

If adjustments to a deposition parameter are desirable, several alternatives are available, either individually or in combination with other parameters. For example, the deposition temperature, deposition power density, deposition power, deposition current, deposition voltage, deposition atmosphere flow rate and deposition atmosphere pressure may all be adjusted to affect the density of the near-substrate region of the molybdenum layer. The deposition atmosphere may typically be an Argon gas. As described in detail below, tuning the Argon pressure in the deposition chamber may directly affect the molybdenum layer density, and therefore, directly affect sodium diffusion in subsequent fabrication steps.

Alternatively, if the density of the molybdenum layer is close to, but not, precisely within tolerances, adjustments may be made to the composition or structure of the subsequent CIGS active layer to compensate for sodium diffusion irregularities expected to be caused by the slightly out of tolerance molybdenum density (Step 222). Thus, the desired sodium diffusion and final device characteristics may be monitored and/or controlled by monitoring the density of the molybdenum in the near-substrate region and substantially contemporaneously controlling subsequent molybdenum or CIGS deposition parameters. The process as illustrated on FIG. 2 is completed by depositing a CIGS layer (Step 224). The process of fabricating an actual device may include the deposition of other layers including, but not limited to, window layers, buffer layers, front contacts and numerous other production steps.

Thus, the methods disclosed above may be implemented to address the problem of variations in CIGS PV production consistency resulting from sodium diffusion irregularity by providing a manufacturing-compatible method to monitor the near-substrate molybdenum density and use this information as; 1) an optical signature to indicate 'good' or 'bad' molybdenum, 2) a feedback control on the molybdenum deposition process and 3) as a feed forward control for CIGS processing to adjust the active layer to changes in the sodium diffusion caused by variations in the near-substrate molybdenum density. An alternative use of the methods and apparatus disclosed herein is the monitoring of the uniformity of molybdenum density across the width and/or the length of the SLG substrate. Full substrate monitoring or selective sampling across various regions of a substrate may be accomplished using multiple optical probes across the width of the moving SLG substrate, or by a single probe that scans across the SLG substrate as it moves through the deposition chamber. Uniformity may be an important and challenging aspect of thin film PV module manufacturing.

The methods described herein may be implemented using conventional commercial PV fabrication equipment having a few key modifications. In particular, the deposition of a molybdenum thin film may be accomplished in any suitable deposition chamber which is modified to allow optical probing as described herein. One non-limiting example of a sputter deposition chamber suitable for implementing the described methods is schematically illustrated in FIG. 3.

Figure 3:
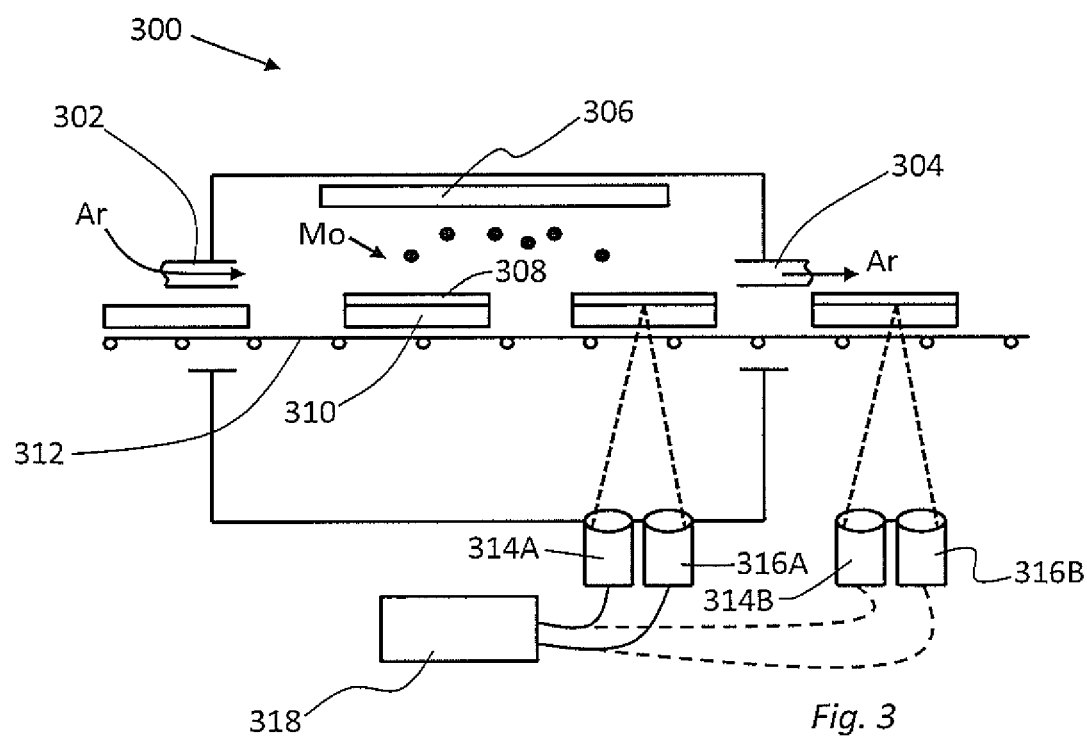
FIG. 3 illustrates a simplified schematic diagram of a deposition chamber as disclosed herein.

The FIG. 3 deposition chamber 300 includes a gas inlet 302 and gas outlet 304 through which a deposition atmosphere (typically Argon) may flow. The gas inlet and outlet are associated with appropriate vacuum pump and valve apparatus to provide for the control of the desired level of partial vacuum within the chamber 300. The deposition chamber 300 may also include a molybdenum target 306 mounted to a sputter gun from which molybdenum atoms are sputtered and then deposited upon the substrates 310 within the chamber. As deposition proceeds, a thin film of molybdenum 308 may be deposited on the glass substrate 310. As noted above, the density and other physical characteristics of the molybdenum layer 308 may be changed by modifying various deposition parameters, including, but not limited to, deposition temperature, deposition power density, deposition power, deposition current, deposition voltage, deposition atmosphere flow rate and deposition atmosphere pressure.

The deposition chamber may also include a substrate transport system 312, which may be a conveyor or similar apparatus configured to convey substrates through the chamber and on to subsequent processing. The chamber 300 may also include or be associated with a light source 314 and a detector 316. Either or both the light source and detector may incorporate wavelength-selective elements such as a spectrometer, prism, low-pass filter, high-pass filter, band-pass filter, liquid-crystal filter, or similar elements. Wavelength selective elements may be required to perform spectroscopic measurements. There are many suitable ways to accomplish spectroscopic measurement. One representative, but non-limiting, method is described in co-owned U.S. patent application Ser. No. 12/237,452, which application is incorporated herein for all matters disclosed therein and in particular for all teaching concerning the optical analysis of materials. The method described in the Ser. No. 12/237,452 application uses rapid modulation of photodiodes of different wavelengths to provide spectral information through the time variation of the optical detector signal.

As shown in FIG. 3 the light source and detector may be situated to optically communicate with the interior of the chamber through suitable windows (see 314A and 316A), or light may be conveyed to and from the chamber through optical fibers, light pipes or other optical transmission means. Alternatively, the light source and detector may be situated downstream from the chamber (see 314B and 316B) and associated with optical fibers, light pipes or other optical transmission means if desired. In both configurations, the light source 314 and detector 316 are oriented to transmit light to and collect light from the near-substrate region of the molybdenum layer 310 for optical analysis as described herein.

The light source and detector may be in electrical or optical digital communication with a processor such as a dedicated control system computer 318. The processor may control the output from the light source, and receive data from the detector. From the data, the processor can calculate the density of the near-substrate molybdenum and if necessary control deposition parameters as described herein. The processor may further control downstream processes including, but not limited to, CIGS layer compositions and CIGS layer deposition parameters to compensate for any sodium diffusion irregularities expected in view of measured molybdenum layer densities.

EXAMPLES

The following examples are provided for illustrative purposes only and are not intended to limit the scope of the invention.

Example 1

A series of molybdenum thin films may be sputtered onto SLG substrates with a DC power of 650 Watt and an Ar flow rate of 50 sccm. The total film thicknesses may be in the range of 0.40-0.55 µm. The 6"×6" substrates may be scanned in front of the 2"×10" target in order to cover the whole substrate area. Each molybdenum film may be deposited with two substrate scans with the same scan speed. There may be no external heating of the substrate. The process variable of Argon gas pressure ($p_{Ar}$) was varied in the range of 6-20 mTorr.

Figure 4:
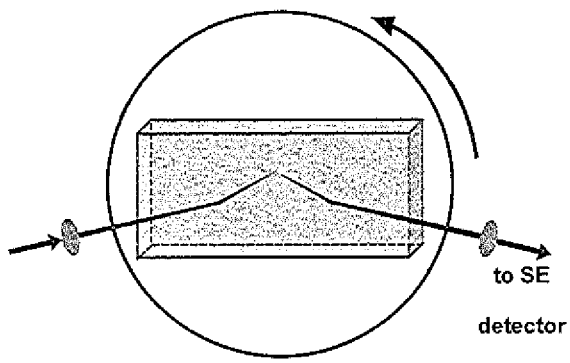
FIG. 4 illustrates a schematic diagram showing an ellipsometry based optical probe configuration.

After deposition, the molybdenum/SLG samples were characterized by Ex situ spectroscopic ellipsometry (SE) in the photon energy range of 0.75-3.6 eV where SLG is transparent. SE may be sensitive to surface non-idealities, such as an oxide layer or surface roughness. Improper treatments of the surface layer may result in large errors in the deduced optical properties of the underlying film. The film/glass interface prepared as described above was found to be almost free of these non-idealities. Therefore, through-the-glass geometry was selected for the SE measurements as shown in FIG. 4. The molybdenum films were found to be optically anisotropic, so SE measurements at multiple orientations were needed to obtain both the ordinary and extraordinary dielectric functions. This was accomplished by fixing the sample on a rotatable holder. At each orientation, anisotropic SE data were taken at angles of incidence (AOI) from 45 to 70°. Focusing optics were used to eliminate the beam reflected at the SLG/air interface from the probing beam reflected at the SLG/molybdenum interface, as these two beams are optically incoherent.

In SE analyses, it was found that uni-axial anisotropy was sufficient to model the molybdenum films which exhibit clear in-plane optical anisotropy. Therefore, two sets of complex dielectric functions, the ordinary one $\in_o$ and the extraordinary one $\in_e$, were needed to describe each molybdenum film. The anisotropic SE data taken at multiple orientations and AOIs for each sample were analyzed together in order to extract its $\in_o$ and $\in_e$ simultaneously with good confidence limits. The resulting optical properties are plotted in FIG. 5.

Figure 5:
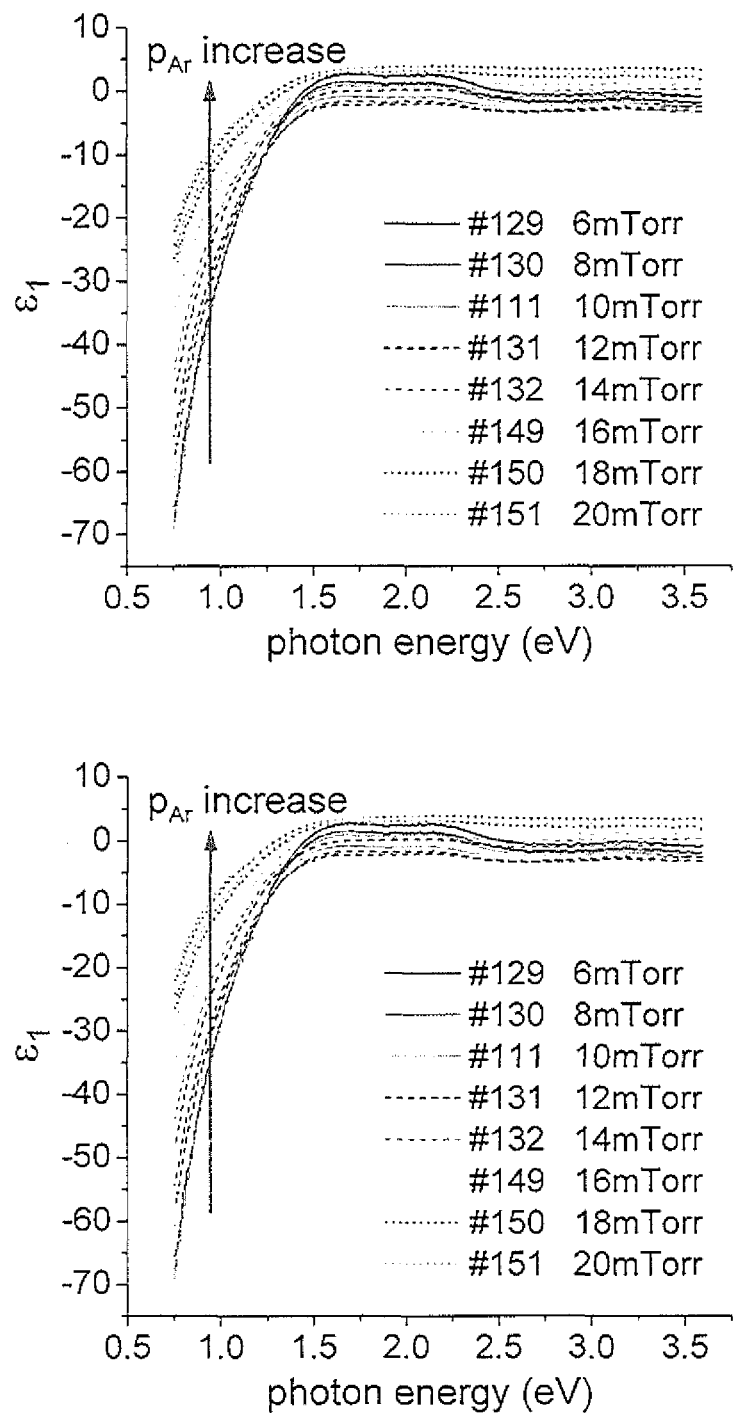
FIG. 5 illustrates a graph representation of two sets of complex dielectric functions $\in$, ordinary $\in_o$ and extraordinary $\in_e$, as determined by ellipsometry for the near-substrate region of eight molybdenum films prepared under different argon pressures ranging from 6 to 20 mTorr.

As may be seen from FIG. 5 that both $\in_o$ (FIG. 5A) and $\in_e$ (FIG. 5B) vary with $p_{Ar}$. In general, high $p_{Ar}$ molybdenum films are optically less anisotropic, indicated by smaller difference between their $\in_o$ and $\in_e$ compared to low $p_{Ar}$ films. Another difference between various $p_{Ar}$ molybdenum films, however, exists in the amplitudes of their dielectric functions. This is more clearly observed in $\in_2$ in FIG. 5B.

In the classical theory of materials optical properties, $\in$ may be expressed as a sum of a series of Lorentzian oscillators:

$$\varepsilon(E) = \varepsilon_1^\infty + \sum_n \frac{A_n}{(E_n^2 - E^2) - i\Gamma_n E} \quad (I)$$

where E is photon energy; $\varepsilon_1^\infty$ is the contribution to $\varepsilon_1$ from the oscillators located at photon energies much higher than the studied spectral range; $A_n$, $E_n$, and $\Gamma_n$ are the amplitude, resonance energy, and the broadening of the $n^{th}$ oscillator. A similar expression exists as deduced from modern quantum theory of materials optical properties. It should be noted that $E_n$ and $\Gamma_n$ have different physical meanings in these two theories, but in either case, $A_n$ tends to be proportional to the number of atoms per unit volume, or the density of the material.

As is for typical metals, the dominant feature in FIG. 5 is the free electron absorption (<1.2 eV), corresponding to a Lorentzian oscillator in Eq. (1) with $E_n=0$, or the Drude oscillator. In this case, neglecting $\varepsilon_1^\infty$ as it is usually much smaller than the Drude oscillator, the negative amplitude in $\varepsilon_1$ or the positive amplitude in $\varepsilon_2$ is proportional to $A_n$, as well as the molybdenum film density $\rho_{Mo}$. Above 1.2 eV, two critical point (CP) structures, with resonance energies located at ~1.7 and 2.4 eV respectively, are observed. In these two cases, $A_n$ cannot be estimated from $\varepsilon_1$, because of the non-negligible contribution of $\varepsilon_1^\infty$, but can be estimated from the amplitude of $\varepsilon_2$. It is observed that in all the main structures in $\varepsilon$ described above, the amplitudes in both $\varepsilon_0$ and $\varepsilon_e$ decrease significantly, indicating a consistent and significant decrease in $\rho_{Mo}$, with increasing $p_{Ar}$. It should also be noted that all the molybdenum films in FIG. 5 are highly absorbing, with the calculated 1/e penetration depth in this photon energy range no more than 27 nm. Therefore, the optical properties and the associated indication in $\rho_{Mo}$ may only apply to the near-substrate part of the molybdenum films.

To confirm the SE indication of $\rho_{Mo}$ determined optically as described above, the microstructure and morphology of selected molybdenum films were examined by high-angle-annular-dark-field scanning transmission electron microscopy (HAADF STEM). An FEI Tecnai F20-UT microscope operating at 200 kV was used for imaging. Cross sectional TEM samples were prepared by focused ion beam technique (FIB) using a FEI Nova200 dual beam FIB system. The intensity of a HAADF STEM image is proportional to the atomic number and the thickness of the film. Because the only element probed here is molybdenum, there is only one atomic number for all the samples; and the TEM sample prepared by FIB have rather uniform thickness, the intensity of HAADF STEM images can then be related to the local density of molybdenum in the films—lower intensity indicates lower density. It can be seen from the HAADF STEM images shown in FIG. 6 that the near-substrate $\rho_{Mo}$ of the $p_{Ar}=6$ mTorr molybdenum film is significantly higher than that of the $p_{Ar}=20$ mTorr molybdenum film, consistent with the SE results described above. It is also noticeable that within a specific molybdenum film, local $\rho_{Mo}$ decreases with distance from the SLG substrate.

Figure 6:
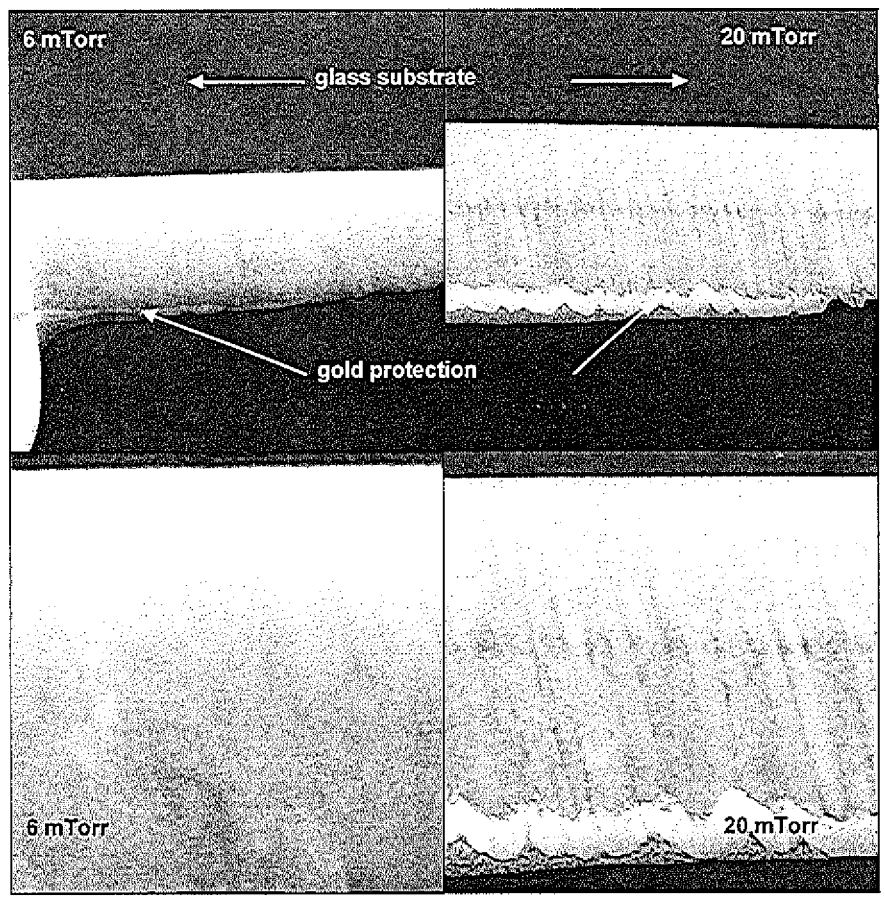
FIG. 6 illustrates a set of high-angle-annular-dark-field scanning transmission electron microscopy images of the two molybdenum films prepared under different argon pressures of FIG. 5.

In the fabrication of CIGS solar cells, the molybdenum layer may act as a barrier to sodium diffusion from SLG into the absorber layer grown on top of molybdenum/SLG. The diffusion coefficient may be inversely dependent on $\rho_{Mo}$. Additionally, as seen in FIG. 6, the near-substrate part is the densest in a specific molybdenum film, and thus will be essentially the bottle neck for sodium diffusion. Therefore, the near-substrate $\rho_{Mo}$, which may be determined using a simple optical probe as shown in FIG. 5, may have an important effect in determining the sodium diffusion. Therefore, in situ optical diagnostics may be applied for process monitoring and optimization of the deposition of molybdenum for CIGS solar cells or other types of cells having a molybdenum contact and featuring sodium diffusion into the active layer.

Example 2

Figure 7:
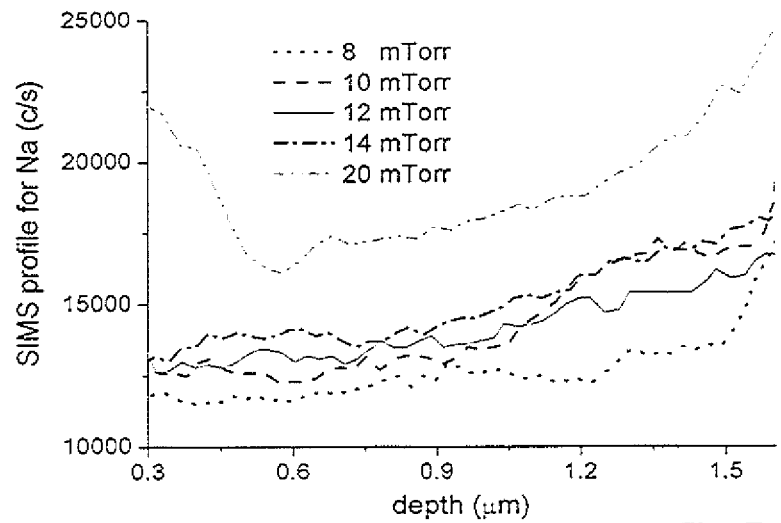
FIG. 7 illustrates a graph representation of the results of secondary ion mass spectroscopy (SIMS) to determine the sodium distribution in CIGS films deposited on molybdenum back contact layers, where the molybdenum layers were deposited under different argon pressures.

To verify the effect of near-substrate $\rho_{Mo}$ on sodium diffusion, standard CIGS layers were grown by the three-stage method with identical deposition parameters on selected molybdenum/SLG samples from Example 1. The resulting CIGS films were depth profiled using secondary ion mass spectroscopy (SIMS) to determine the sodium distribution. The SIMS results plotted in FIG. 7 not only show the expected trend of increasing sodium concentration with increasing $p_{Ar}$, and hence decreasing $\rho_{Mo}$, but also vary on a relative quantitative scale similar to that shown in FIG. 5. This appears to demonstrate a correlation between the optical properties in FIG. 5 and the sodium distribution of FIG. 7.

Example 3

Simulated

Figure 8:
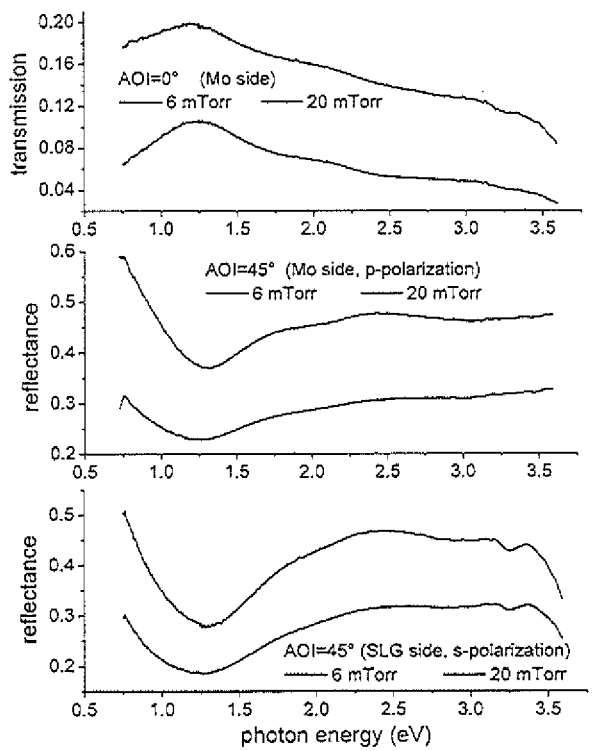
FIG. 8 is a graph representation of simulated transmission and reflection curves for selected photon energies as applied to the near-substrate region of two thin films of molybdenum deposited under different argon gas pressures.

As noted above, a proper amount of sodium diffusion may be important for the fabrication of high efficiency CIGS solar cells. The observations above provide an optical diagnostic for the optimization and control of sodium diffusion. To demonstrate such capabilities, the normal incidence (AOI=0°) transmission from the molybdenum side, the AOI=45° reflectance from the molybdenum side for p-polarized light, and the AOI=45° reflectance from the back side of the SLG substrate for s-polarized light are simulated in FIG. 8, assuming a sample structure of 20 nm molybdenum layer deposited on SLG and using the optical properties in FIG. 5. It can be seen that in all the cases of FIG. 8, the difference between the two samples deposited at different argon pressures tends to be significant, and hence, detectable by the optical diagnostics based on intensity or transmission measurements. The overall sensitivity of a non-contact optical measurement may be enhanced if desirable by using diagnostics based on polarization measurements, such as SE with two measured quantities.

Various embodiments of the disclosure may also include permutations of the various elements recited in the claims as if each dependent claim was a multiple dependent claim incorporating the limitations of each of the preceding dependent claims as well as the independent claims. Such permutations are expressly within the scope of this disclosure. Several embodiments have been particularly shown and described. It should be understood by those skilled in the art that changes in the form and details may be made to the various embodiments disclosed herein without departing from the spirit and scope of the disclosure and that the various embodiments disclosed herein are not intended to act as limitations on the scope of the claims. Thus, while a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions and sub-combinations as are within their true spirit and scope.

What is claimed is:

1. A method of measuring a density of a near-substrate region of a molybdenum layer deposited on a surface of a glass substrate, the method comprising:

directing light through the glass substrate to the near-substrate region of the molybdenum layer;

detecting an optical property of the near-substrate region of the molybdenum layer based on the light that interacts with the near-substrate region of the molybdenum layer; and determining a density of the near-substrate region of the molybdenum layer based on the detected optical property, wherein the determined density is a number of atoms per unit volume.

2. The method according to claim 1, wherein the light has one or more predetermined wavelengths.

3. The method according to claim 1, wherein the optical property is at least one of light polarization or light intensity.

4. The method according to claim 1, wherein the optical property is detected by at least one of non-spectroscopic ellipsometry, non-spectroscopic reflectivity, non-spectroscopic transmission, spectroscopic ellipsometry, spectroscopic reflectivity, or spectroscopic transmission.

5. The method according to claim 1, wherein the light is directed through the glass substrate to the near-substrate region of the molybdenum layer as the glass substrate moves in a fabrication process line.

6. A method of fabricating a photovoltaic device, the method comprising:

depositing a molybdenum layer on a surface of a glass substrate;

directing light through the glass substrate to a near-substrate region of the molybdenum layer;

detecting an optical property of the near-substrate region of the molybdenum layer based on the light that interacts with the near-substrate region of the molybdenum layer; and determining a density of the near-substrate region of the molybdenum layer based on the detected optical property, wherein the determined density is a number of atoms per unit volume.

7. The method according to claim 6, further comprising controlling a molybdenum deposition parameter based upon the determined density of the near-substrate region of the molybdenum layer.

8. The method according to claim 7, further comprising:

depositing an active absorber layer above the molybdenum layer; and controlling sodium diffusion through the molybdenum layer to the active absorber layer by controlling the density of the near-substrate region of the molybdenum layer via the molybdenum deposition parameter.

9. The method according to claim 8, wherein the active absorber layer is a CIGS layer.

10. The method according to claim 7, wherein the controlled molybdenum deposition parameter is at least one of deposition temperature, deposition power density, deposition power, deposition current, deposition voltage, deposition atmosphere flow rate, or deposition atmosphere pressure.

11. The method according to claim 7, wherein the controlled molybdenum deposition parameter comprises argon pressure.

12. The method according to claim 7, further comprising controlling a density of a subsequently deposited molybdenum layer by controlling the molybdenum deposition parameter.

13. The method according to claim 6, further comprising controlling at least one of a CIGS layer composition or a CIGS layer deposition parameter based on the determined density of the near-substrate region of the molybdenum layer.

14. The method according to claim 6, wherein the light has more than one predetermined wavelength.

15. The method according to claim 6, wherein the optical property is at least one of light polarization or light intensity.

16. The method according to claim 6, wherein the optical property is detected by at least one of non-spectroscopic ellipsometry, non-spectroscopic reflectivity, non-spectroscopic transmission, spectroscopic ellipsometry, spectroscopic reflectivity, or spectroscopic transmission.

17. The method according to claim 6, wherein the light is directed through the glass substrate to the near-substrate region of the molybdenum layer as the glass substrate moves in a fabrication process line.

18. A system comprising:

a light source configured to illuminate a near-substrate region of a molybdenum layer deposited on a glass substrate;

a detector configured to receive light from the light source after the light interacts with the near-substrate region of the molybdenum layer, and to detect an optical property of the near-substrate region of the molybdenum layer based on the received light; and a processor configured to communicate with the detector, the processor being further configured to determine a density of the near-substrate region of the molybdenum layer based on the detected optical property, wherein the determined density is a number of atoms per unit volume.

19. The system according to claim 18, wherein the processor is further configured to control a deposition parameter based on the determined density of the near-substrate region of the molybdenum layer.

20. The system according to claim 19, wherein the controlled deposition parameter is at least one of deposition temperature, deposition power density, deposition power, deposition current, deposition voltage, deposition atmosphere flow rate, or deposition atmosphere pressure.

21. The system according to claim 18, wherein the light has more than one specified wavelength.

22. The system according to claim 18, wherein the optical property is at least one of light polarization or light intensity.

23. The system according to claim 18, wherein the optical property is detected by at least one of non-spectroscopic ellipsometry, non-spectroscopic reflectivity, non-spectroscopic transmission, spectroscopic ellipsometry, spectroscopic reflectivity, or spectroscopic transmission.

24. The system according to claims 18, further comprising a substrate transport system configured to permit the light to be transmitted through the glass substrate to illuminate the near-substrate region of the molybdenum layer as the glass substrate moves in a fabrication process line.

* * * * *